United States Patent [19]

Litsche

[11] Patent Number: 5,240,678
[45] Date of Patent: Aug. 31, 1993

[54] DEVICE FOR TRANSPORTING CONTAINERS FILLED WITH A LIQUID

[75] Inventor: Mario Litsche, Nellmersbach, Fed. Rep. of Germany

[73] Assignee: Eastman Kodak Company, Rochester, N.Y.

[21] Appl. No.: 732,249

[22] Filed: Jul. 18, 1991

[30] Foreign Application Priority Data

Jul. 20, 1990 [DE] Fed. Rep. of Germany ....... 4023184

[51] Int. Cl.⁵ ............................................. G01N 21/00
[52] U.S. Cl. ........................................ 422/64; 422/65; 422/67
[58] Field of Search ............................... 422/63, 65, 67

[56] References Cited

U.S. PATENT DOCUMENTS

| | | | |
|---|---|---|---|
| 3,768,526 | 10/1973 | Sanz et al. | 422/63 |
| 4,478,095 | 10/1984 | Bradley et al. | 73/864.21 |
| 4,604,363 | 8/1986 | Newhouse et al. | 436/177 |
| 4,798,095 | 1/1989 | Itoh | 73/863.01 |
| 4,798,703 | 1/1989 | Minekane | 422/65 |
| 4,816,418 | 3/1989 | Mack et al. | 436/518 |
| 4,927,603 | 5/1990 | Fischer et al. | 422/67 |
| 5,008,082 | 4/1991 | Shaw | 422/65 |

FOREIGN PATENT DOCUMENTS 2632035 3/1977 Fed. Rep. of Germany.

Primary Examiner—Robert J. Warden
Assistant Examiner—Krisanne M. Thornton
Attorney, Agent, or Firm—Peter J. Bilinski

[57] ABSTRACT

An analyzer is described which includes an input station for trays carrying containers filled with body fluids. It consists of a plurality of tray tracks arranged side by side and whose central axes intersect in a point which is vertically aligned with the pivot point of a pivotally arranged transporter. The transporter can be aligned with any of the tray tracks. By means of a tray movement member the tray can be transported from the input station to the processing stations and back. The exits of the tray tracks are associated with retaining means which are controlled in the same way as the stepper motors in response to sensors and a microprocessor.

34 Claims, 8 Drawing Sheets

DEVICE FOR TRANSPORTING CONTAINERS FILLED WITH A LIQUID

FIELD OF THE INVENTION

The invention relates to a device for transporting in an analyzer containers filled with a liquid and arranged in a tray, in particular test tubes filled with a body fluid, from an input station to a processing station and back.

BACKGROUND OF THE INVENTION

Various analyzers are known which are provided with automatic transport means and can process a number of samples or body fluids to be examined.

From DE-A-26 32 035 an apparatus is known for automatically advancing samples to be examined and contained in test tubes to a processing station of an analyzer and back. A plurality of test tubes are carried by an elongate tray with the trays themselves being held in a magazine. Each tray is associated with a locking means which is selectively controllable and can be released in a tray removal station. A first advancing means moves the magazine from an input station to said tray removal station. Removal of the trays is effected by a second advancing means arranged normal to said first means and advancing the trays filled with test tubes to the processing station. The two advancing means are provided with conveyor belts driven by reversible stepper motors that can be selectively advanced. The first advancing means comprises two toothed conveyor belts and a sliding path therebetween, the teeth of the belts engaging with corresponding teeth arranged at the lower side of the tray magazine. The second advancing means is provided with a conveyor belt having a drive pin engaging a slot at the lower side of the tray.

Another apparatus is known from DE-A-32 42 459 using a sample distributor having a number of carriers for test tubes arranged on a round rotatable plate. Insertion of the carriers equipped with test tubes is effected through an input and removal opening at the front side of the apparatus with the carrier being put on plugs arranged on the plate's rim. Subsequently, the carriers are advanced together with the test tubes to a processing/aspirator station, which is effected by rotating the plate by means of a microprocessor controlled drive mechanism.

Commonly-owned EPA 356,250 published Feb. 28, 1990 by Shaw and entitled "Analyzers Using Linear Sample Trays With Random Access", discloses similar tray-processing analyzer, except that the input tracks for the trays are preferably parallel to each other. Also each track has a separate conveying means for that track. (The corresponding U.S. patent application Ser. No. 236,588 filed Aug. 25, 1988 is now allowed.) Although such an arrangement has proven to be highly effective, it would be advantageous to provide the same result but with fewer positively-acting drive motors for the analyzing means.

SUMMARY OF THE INVENTION

It is the object of the present invention to provide an apparatus of the generic type which is of uncomplicated design and permits simple loading and easy access to containers arranged in the apparatus. The processing rate is to be increased considerably in order to meet the requirements of a fast and reliable diagnosis.

The above object is attained in that for receiving the trays the input station consists of a plurality of tray tracks arranged side by side and whose central axes intersect in a point which is vertically aligned with the pivot point of a pivotally arranged transporter that can be aligned with any of the tray tracks.

Further features and advantages will be described in detail with reference to an embodiment of the invention shown in the drawing and claimed in the subclaims.

DESCRIPTION OF THE PREFERRED EMBODIMENTS

Figure 1A:
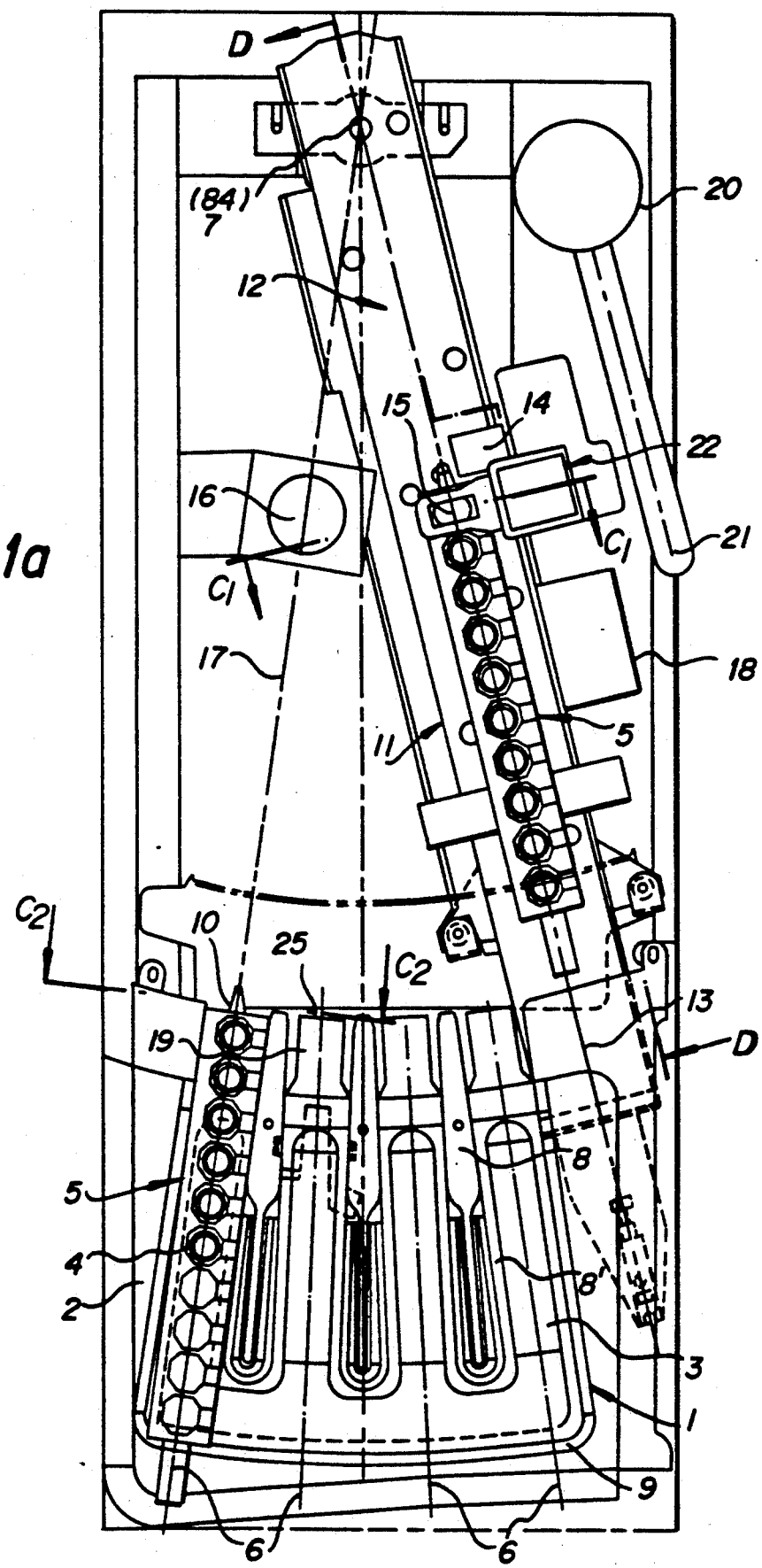
FIG. 1a shows a top view of the device according to the invention including an input station and a transporter.
Figure 1B:
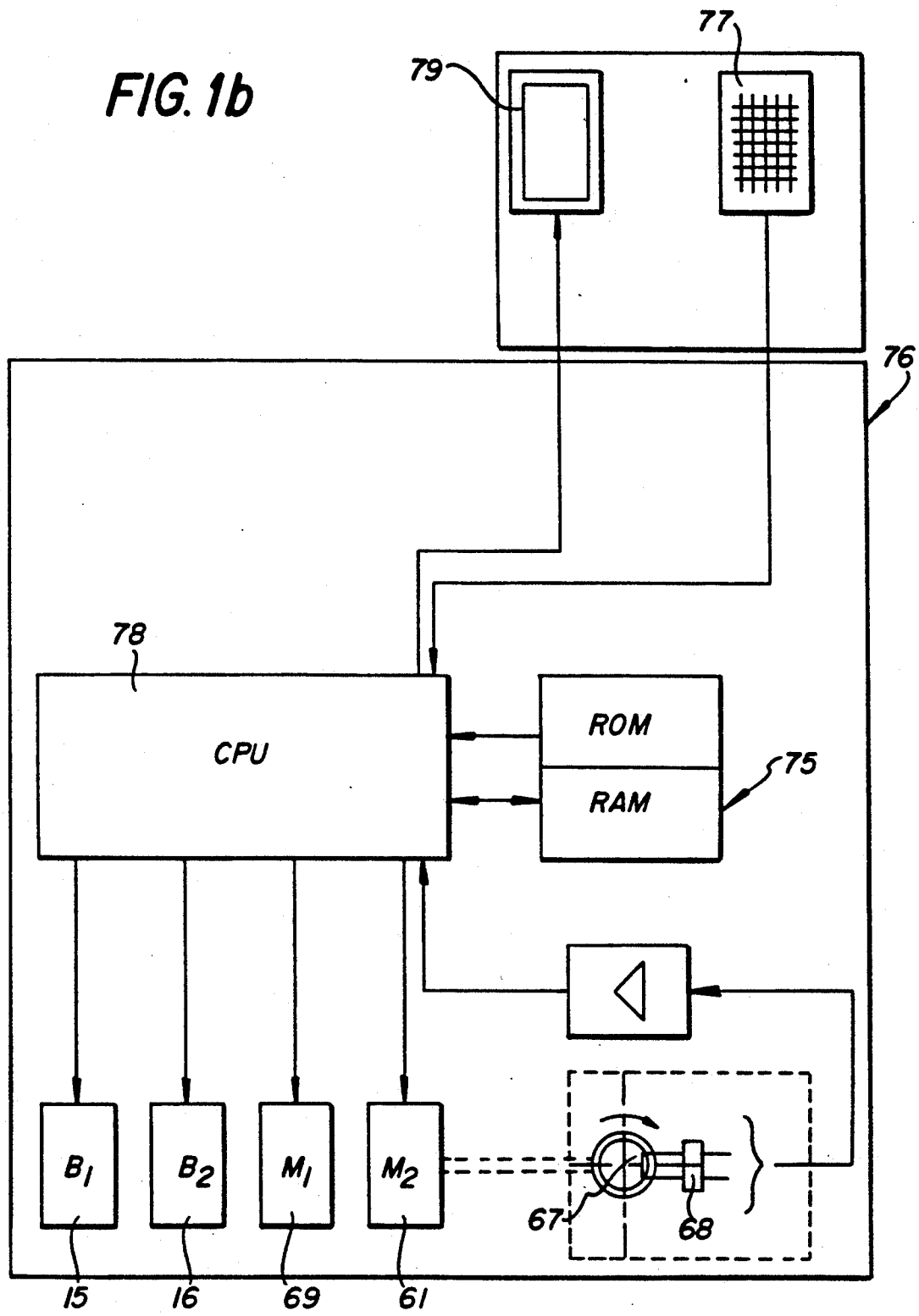
FIG. 1b shows the control unit of the device.
Figure 8:
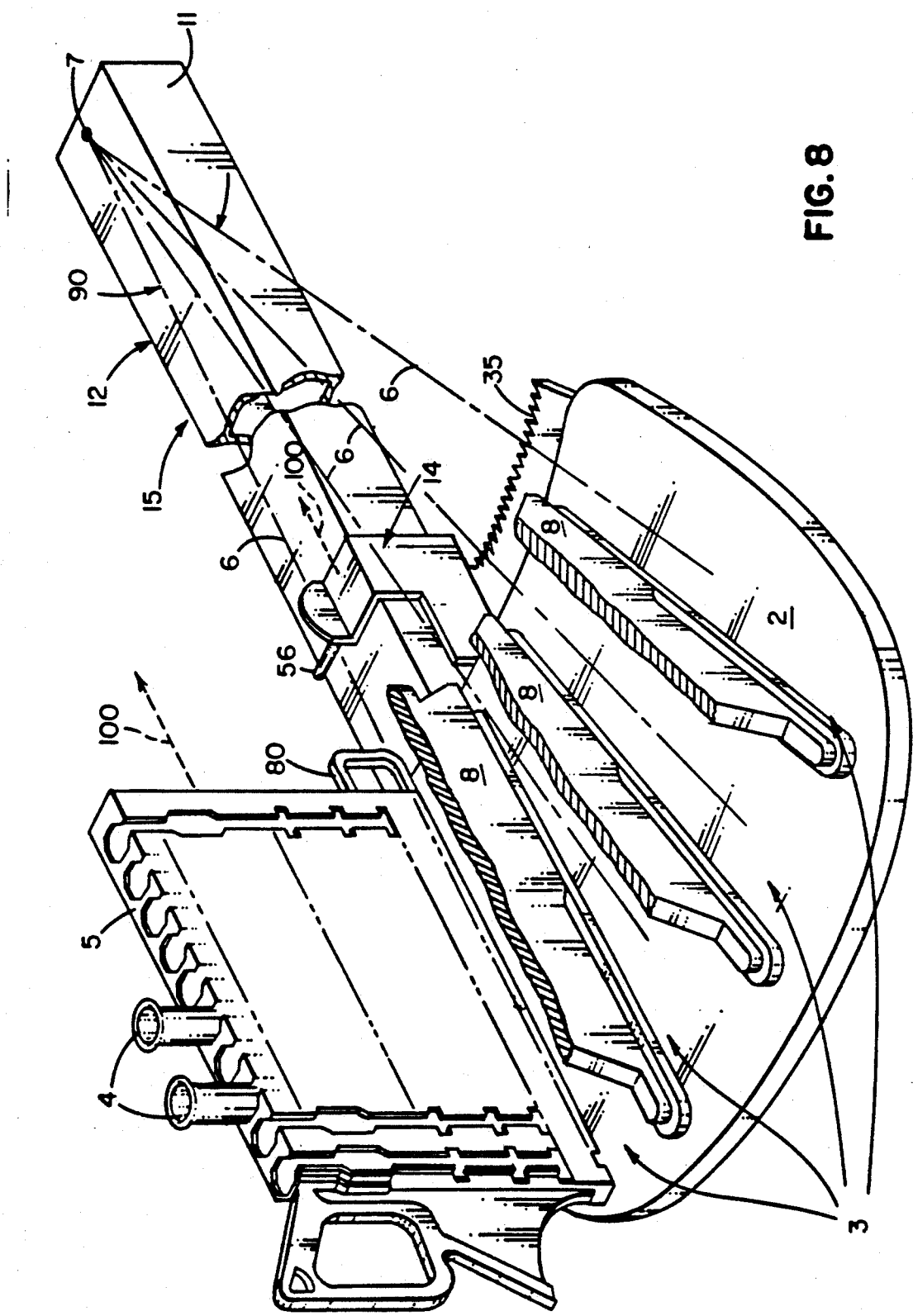
FIG. 8 is a fragmentary perspective view of some of the components illustrated in FIG. 1.

An input station 1 shown in FIGS. 1 and 8 is comprised of four tray tracks 3 arranged side by side on a support plate 2 for receiving trays 5 carrying test tubes 4. The central axes 6 of the tray tracks 3 intersect in a point 7. All tray tracks 3 are separated from one another by partitions 8 and countersunk in the support plate 2 by about twice the height of the widened base (83) of tray 5 (see FIG. 5). The partitions 8 are recessed from the outer border 9 of the input station 1 and extend as far as their arcuately arranged exits 10. The partitions 8 are wedge-shaped with their widened and rounded end portions facing the outer border 9. The tray tracks 3 show a length and width which are somewhat larger than those of base 83 of each tray 5.

Between input station 1 and intersecting point 7 a transporter 12 is provided which is formed as an elongated housing 11 and can be pivoted about a pivot point 84 the center of which lies directly below point 7. The transporter can be pivoted to any of the tray tracks 3 and aligned with a zero position 13 (FIG. 1) arranged adjacent to the tray tracks 3. The transporter 12 extends as far as the arcuately arranged exits 10 of input station 1. The center of the arc also lies in intersecting point 7.

Figure 5:
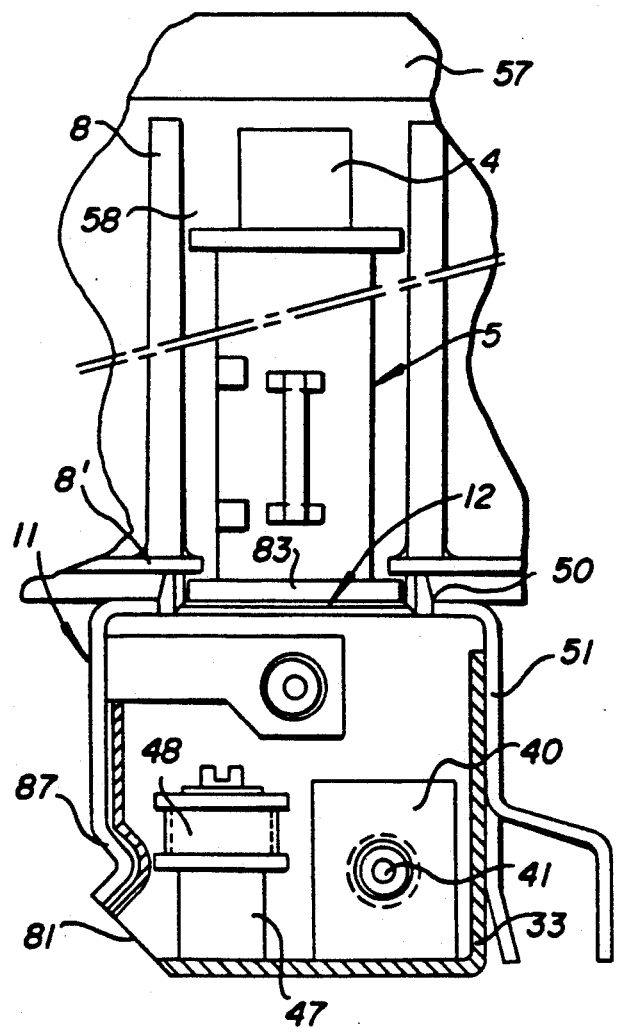
FIG. 5 shows a cross-section along the line C2—C2 in FIG. 1 of the transporter of the device according to FIG. 1 including a passage.

Lateral to the transporter 12, a tray movement member or tray engager 14 (FIGS. 1 and 8) is longitudinally slideable and is used for transporting tray 5 from the input station 1 to a processing station 15 and back. The tray movement member 14 reaches through an elongate opening 81 provided in housing 11 (FIG. 5).

In a processing station 15 an aspirator 20 is provided having a proboscis 21 for removing body fluid from the test tube 4 as well as a detector means 22 for scanning a test tube 4. Processing station 15 is arranged about halfway down the transporter 12 pivoted to its zero position, with the transporter 12 being approximately twice as long as a tray 5. This design permits tray 5 to move to processing station 15 both with its first and last test tube 4 without its trailing end extending into the input station 1.

A second processing station 16 for opening and closing the test tubes 4 is arranged along transporter 12, that is to say in an end position 17 opposed to the zero position 13 which is also halfway down between input station 1 and intersecting point 7. Furthermore, a bar code scanner (18) is provided between processing station 15 or 16 and input station 1 reading the patient's data printed on the test tubes 4.

Each exit 10 of the tray tracks 3 is provided with a retaining means (19) which is disengageable when the transporter 12 is aligned with a tray track 3.

While the input station 1 with its tray tracks 3 is accessible to an operator, the transporter 12 and the processing stations 15 and 16 are covered by a wall 57 within the analyzer Partitions 8 which are somewhat higher than the tray 5 prevent access through passage 58 (see FIG. 5).

Figure 2:
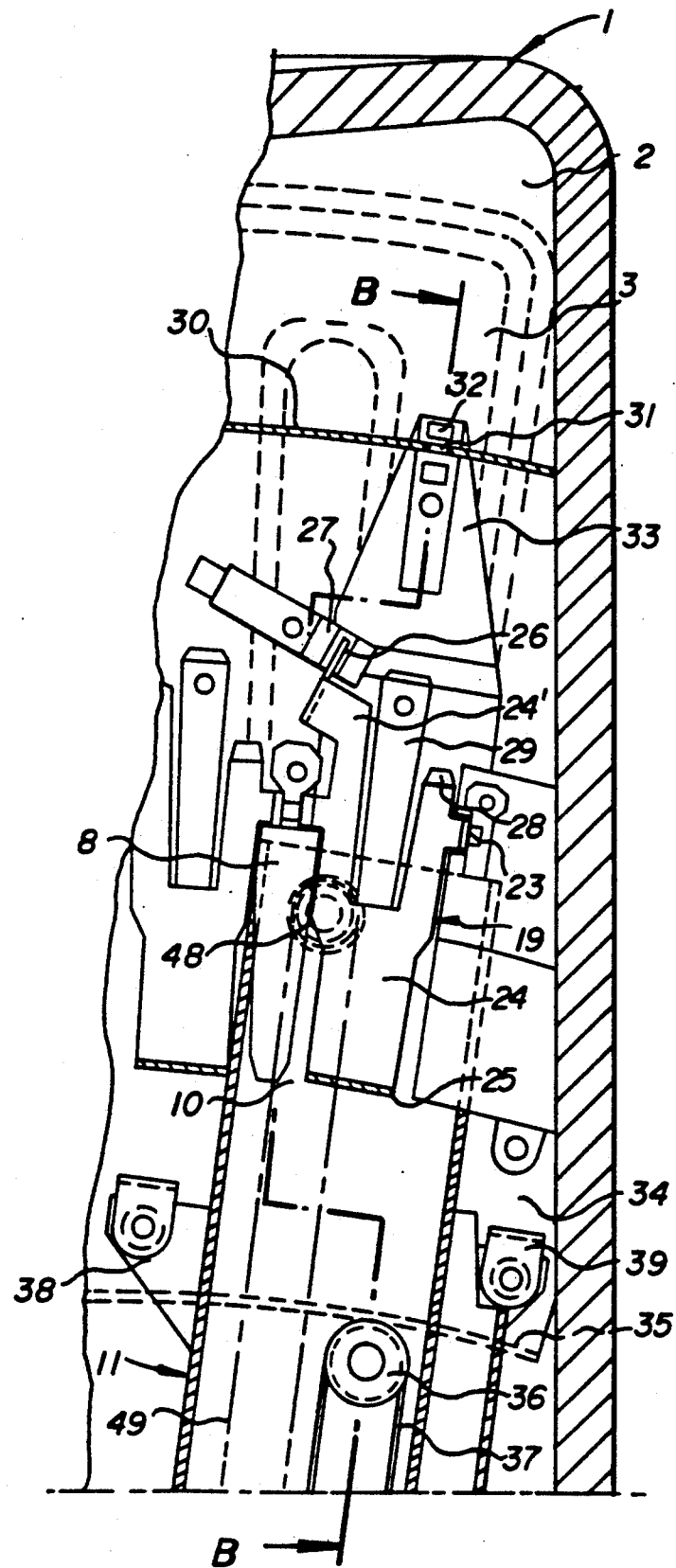
FIG. 2 represents a top view (partly in cross-section) of the input station of the device according to FIG. 1.
Figure 3:
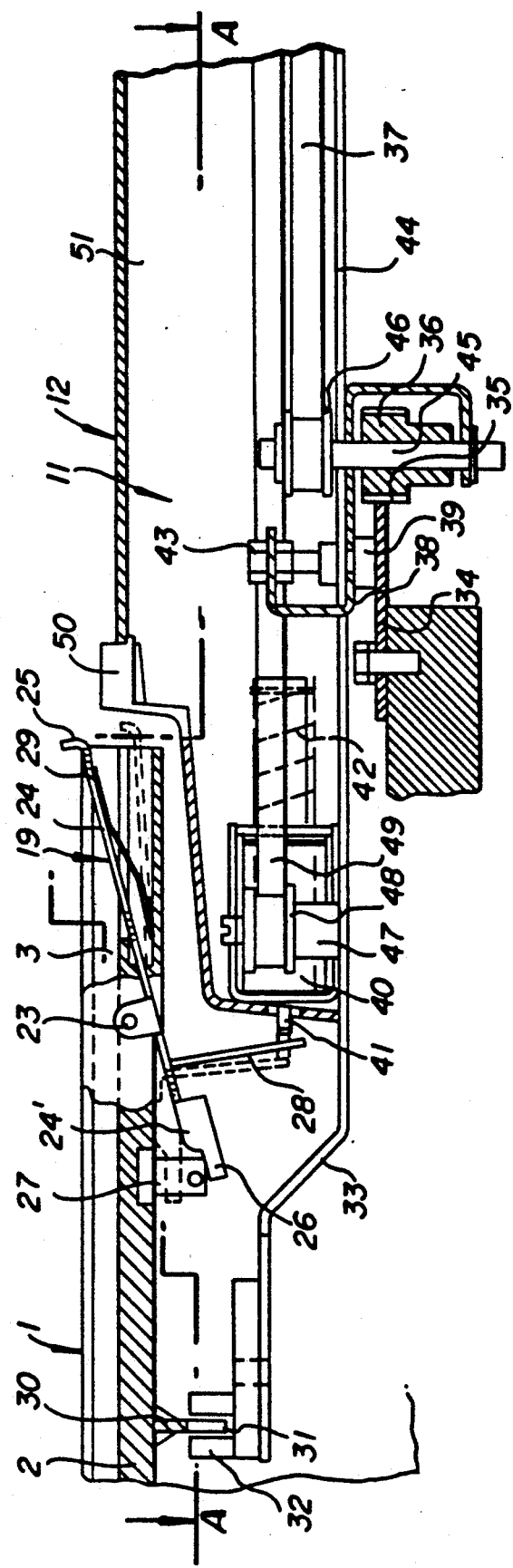
FIG. 3 shows a cross-section along the line B—B in FIG. 2 of the input station of the device according to FIG. 1 including a tray track.

FIGS. 2 and 3 show the retaining means 19 arranged below the support plate 2 of input station 1. Each retaining means 19 is designed as a rocker which is vertically pivotable about an axis of rotation 23. A first rocker arm 24 of retaining means 19 partly extends into tray track 3 and its end portion in the area of an exit 10 is provided with a blocking element 25 for a tray 5. The second rocker arm 24', on the one hand, consists of a blade 26 whose end portion extends into the light path of an optical sensor 27 designed as a light barrier and, on the other, of a finger 28. A leaf spring 29 mounted to the support plate engages said first rocker arm 24 and forces the blocking element 25 into the area of exit 10 of a tray track 3.

Furthermore, beneath the outer end portions of partitions 8 the input station 1 comprises a circularly extending rib 30 having slots 31 associated with the tray tracks 3. Zero position 13 is characterized by two slots. A sensor 32 designed as a light barrier and mounted on an outrigger 33 of transporter 12 is used for scanning slots 31 so as to align transporter 12 with the tray tracks 3 and the zero position.

In the area of the exits 10 and beneath the transporter 12 a support plate 34 is provided having an arcuate rack 35 at its end portion facing the transporter 12. A pinion 36 supported by housing portion 51 engages with said rack 35, with said pinion 36 being connected to a drive mechanism by means of a toothed belt 37. A support bracket 38 which is mounted to housing portion 51 is provided with two supports 39 that slide on the support plate 34 when the housing portion 51 and thus the transporter 12 are pivoted. FIG. 3 shows the retaining means 19 in its first end position to which it is urged by leaf spring 29, blocking element 25 of the first rocker arm 24 extending into exit 10 of an empty tray track 3. In this case, the blade 26 arranged at the other end of the rocker is positioned below the sensor 27 thus uncovering same. When a tray 5 equipped with test tubes 4 is inserted in the tray track 3, the retaining means 19 pivots about axis of rotation 23 to a second position shown in dotted lines in which, on the one hand, the blocking element 25 still extends into the tray track 3 and, on the other, blade 26 covers the sensor 27.

On the outrigger 33 connected to housing 11 an electromagnet 40 is mounted beneath the retaining means 19 which electromagnet when energized moves a plunger 41 along the central axis 6 and thus actuates the finger 28 of retaining means 19. Subsequently, retaining means 19 pivots to its third position and exit 10 of the tray track 3 is disengaged and sensor 27 is uncovered. After de-energizing the electromagnet 40, plunger 41 is returned to its home position shown in the drawing by means of a helical spring 42.

Furthermore, FIG. 3 shows the support plate 34 and the support bracket 38 in connection with one of the two supports 39 having a screw 43 by means of which the housing portion 51 and thus the transporter 12 can be adjusted in height in the region of the exits 10 of input station 1. Support bracket 38 is S-shaped and connected to the bottom portion 44 of housing 11 and, in addition, serves as a bearing for shaft 45 on which pinion 36 and the drive roller 46 for the pivot drive of transporter 12 are arranged. On its outer end, the bottom portion 44 carries the outrigger 33 which in turn carries a shaft 47 with an idler 48 in addition to the electromagnet 40 and sensor 32, said idler 48—together with a toothed belt 49—belonging to a drive mechanism for the tray movement member 14.

A guide 50 for the trays 5 which is associated with each exit 10 of a tray track 3 and consists of guide webs is provided at transporter 12. Also the electromagnet 40 and the idler 48 are accommodated in the housing 11 defining the transporter 12 and are thus protected from fouling.

Figure 4:
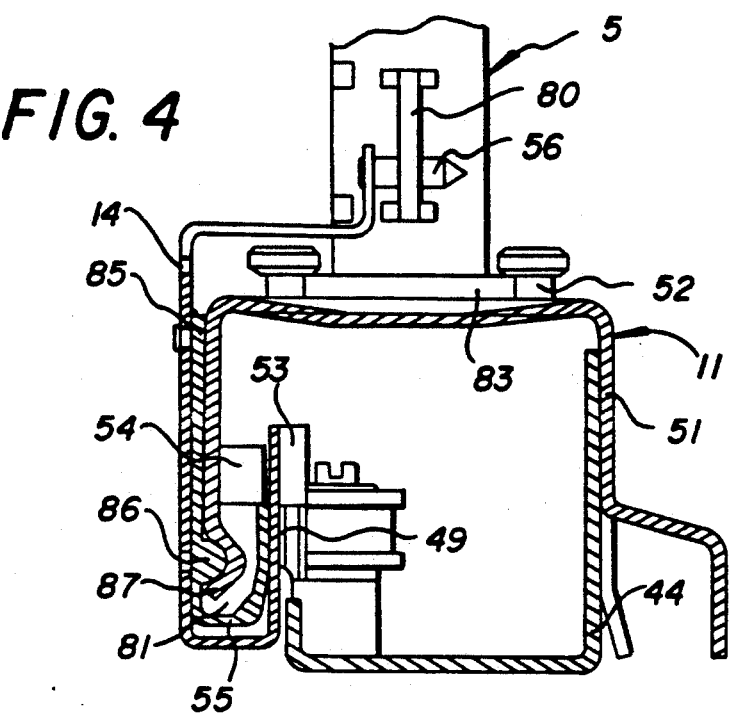
FIG. 4 shows a cross-section along the line C1—C1 in FIG. 1 of the transporter of the device according to FIG. 1.

As shown in FIG. 4, the transporter 12 consists of a rectangularly shaped tubular housing 11 which is substantially closed all-around and is formed of a housing portion 51 of U-shaped cross-section and a bottom portion 44 of L-shaped cross section that are connected so as to define an elongate opening 81.

On both sides of the transporter 12 T-shaped guide posts 52 are arranged between which the widened base 83 of tray 5 is guided. The tray movement member 14 extending into the interior of housing 11 through the elongate opening 81 and connected to the toothed belt 49 by means of a clamping element 53 is mounted to one side of housing 11. Also a bolt 54 and an angular member 55 are connected to clamping element 53. Bolt 54 and angular member 55 rest on a spherical support surface 85 on the inner side of housing portion 51 and on the exterior side thereof, respectively. At its lower end portion, angular member 55 is also provided with a spherical elevation 86 sliding in a prism-shaped guide means 87 of housing portion 51. At the top end of the tray movement member 14 a hook 56 is mounted which above the guide posts 52 extends laterally and horizontally beyond the center of transporter 12 and for advancing tray 5 engages an eyelet 80 provided on the front side of the tray.

FIG. 5 shows the transporter 12 in the region of the exit 10 of a tray track 3. The two laterally arranged guides 50 can be seen on the transporter 12. Behind thereof are shown an interior view of a wall 57 and the partitions 8 of the input station 1 which define a passage 58 through which only trays 5 having a predetermined height and width can reach the transporter. The lower end of the partitions 8 are provided with horizontally extending guide fins 8' which above the widened base 83 of an inserted tray 5 and laterally extend into the tray track 3.

Below the transporter 12 and within the housing 11, respectively, the arrangements of the idler 48 of the drive mechanism of the tray movement member 14 and of the electromagnet 40 can be seen.

Figure 6:
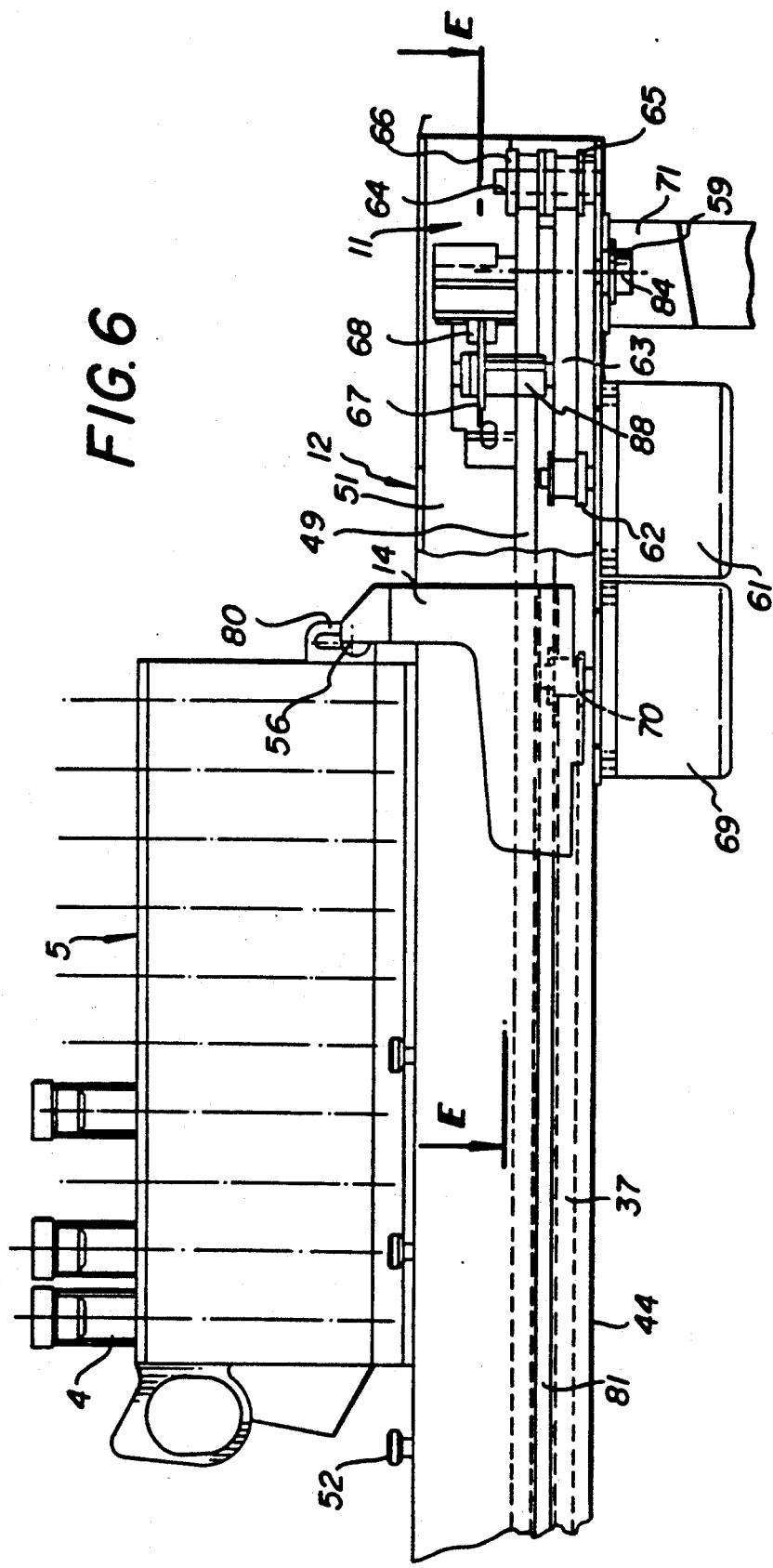
FIG. 6 shows a cross-section along the line D—D in FIGS. 1 and 7 of the transporter of the device according to FIG. 1 including the tray movement member and the drive elements.

FIG. 6 shows the transporter 12 with a tray 5 positioned thereon. Along transporter 12 guide posts 52 which as to their cross-section correspond to said guide fins 8' are arranged in spaced relation to each other so as to define reliable guidance for tray 5 and permit obstacles that may lie in the transporter 12 to be cleared sidewards out of the way by tray 5. This prevents the tray from getting stuck.

Beneath the bottom portion 44 of housing 11 a stepper motor 61 is mounted which by means of a drive gear 62, a toothed belt 63 and a guide roller 65 mounted on shaft 64 drives a drive gear 66 and, thus, by means of toothed belt 49 and the idler 48, the tray movement member 14 (see FIG. 3). On shaft 88 driven by means of the toothed belt 49 an encoder wheel 67 is mounted whose rotary movement is detected by a sensor 68 designed as a light barrier.

Another stepper motor 69 is mounted adjacent stepper motor 61 on the bottom portion 44, said motor 69—by means of drive gear 70 and the toothed belt 37—driving pinion 36 for pivoting transporter 12. When transporter 12/housing 11 is pivoted, it rotates about journal 59 arranged in pivot point 84 in a bearing block 71.

Figure 7:
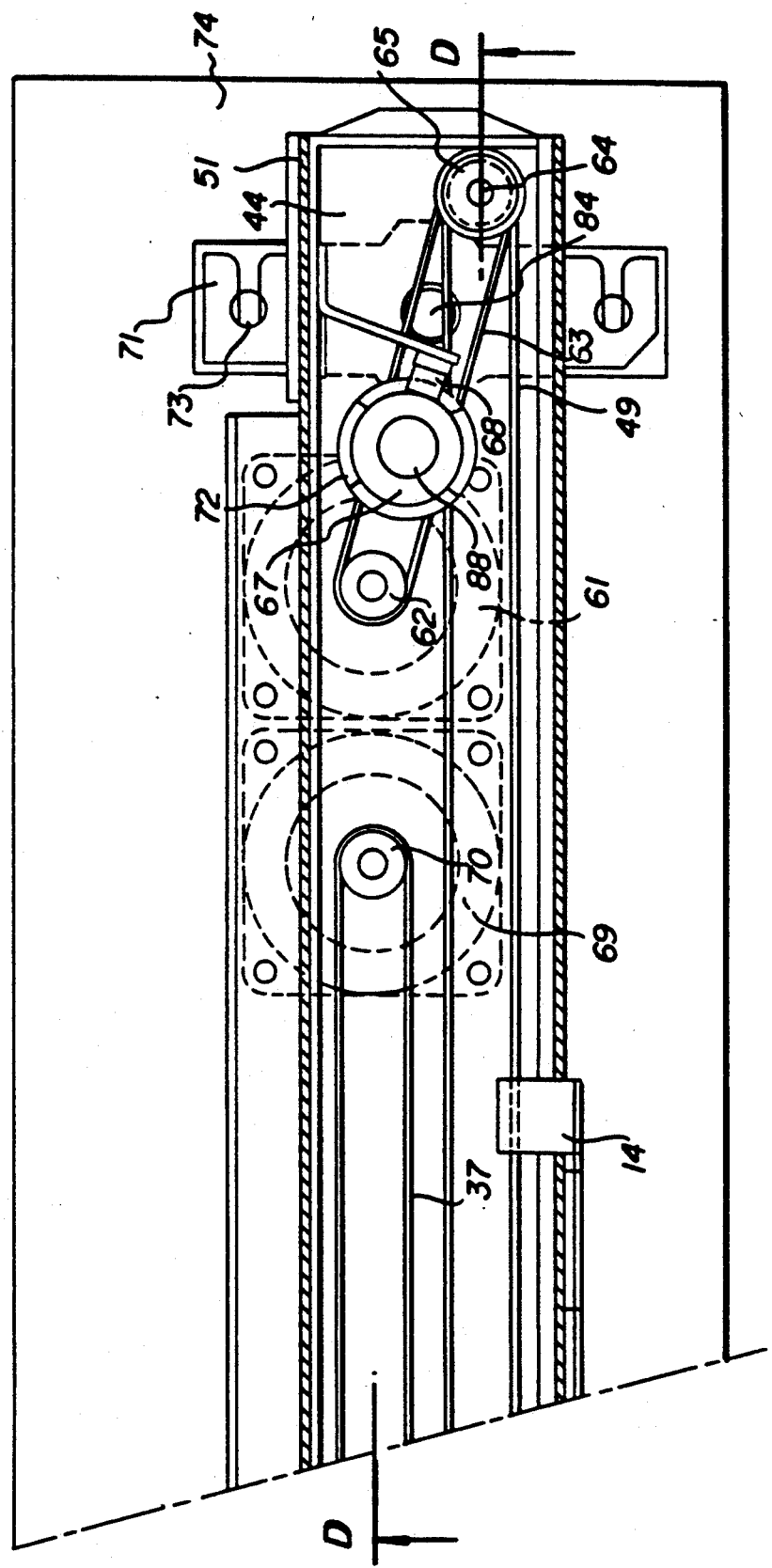
FIG. 7 shows a cross-section along the line E—E in FIG. 6 of the transporter of the device according to FIG. 1 including the drive elements.

FIG. 7 shows the arrangement of the stepper motors 61 and 69 with the drive gears 62 and 70 as well as the toothed belts 37, 49 and 63. The encoder wheel 67 mounted on shaft 88 has opaque and transparent sectors 72 which during rotation of the encoder wheel 67 are scanned by the sensor 68. The number of pulses thus generated is in this case proportional to the movement of the tray movement member 14 along transporter 12.

Furthermore, the structure of bearing block 71 is represented which is mounted to a chassis 74 by means of two screws 73. Also shown is the position of journal 59 for the housing 11.

The device operates as follows:

First, one or several trays 5 equipped with test tubes 4 are placed in the four tray tracks 3 of input station 1. Each test tube filled with a patient's body fluid is provided with specific patient's data and processing instructions which are prepared at the beginning of an examination and transferred to a memory 75 of an electronic control unit 76 of the analyzer (see FIGS. 1a and 1b). Upon insertion of trays 5, the number of the tray track 3 and the position of the test tube 4 in tray 5 are added to the aforementioned data by means of the keyboard 77 connected to the control unit 76.

If now by means of the keyboard 77 processing of the body fluids is started, it is effected according to a program stored in the control unit 76 in cooperation with a microprocessor 78. This procedure can individually be preselected by means of the key-board 77, which means that loading the tray track 3 with trays 5 and equipping the trays 5 with test tubes 4 can be performed and altered individually. (See FIG. 1b).

In this way, an analyzer is provided which can be flexibly handled and can process a relatively large amount of samples of body fluids quickly and in any order whatever according to the respective requirements.

After starting the program it is detected whether a tray 5 is present in the selected tray track 3 of the input station. This is done by inquiring the sensor 27 beneath the retaining means 19 shown in FIGS. 2 and 3 which when a tray 5 is present is covered by the blade 26 of retaining means 19. If a tray 5 is present in a tray track 3, the transporter 12 is pivoted, arrow 90, FIG. 8, about journal 59 in the direction of the tray track 3 selected. Pivoting is effected by the stepper motor 69, the drive gear 70, the toothed belt 37 and the pinion 36 meshing with rack 35, FIGS. 3 and 8, the stepper motor 69 being controlled by the microprocessor 78. The position of the transporter 12 is detected on the one hand, by the stepping pulses of the stepper motor 69 and, on the other, by sensing the slots 31 associated with the tray tracks 3 by means of the sensor 32 mounted on the outrigger 33. When the transporter 12 has reached the tray track 3 selected, it pivots in response to its pivoting direction a certain amount beyond said tray track or back in the opposite direction. Said amount is chosen such that the hook 56 of the tray movement member 14, FIGS. 6 and 8, guided at the side of housing 11 can move past the eyelet 80 of tray 5 when said member 14 moves along transporter 12. When during movement of the tray movement member 14 from point 7 to tray track 3 hook 56 is positioned in the area of the central axis of eyelet 80, transporter 12 pivots back to the extent that hook 56 engages the eyelet 80 and transporter 12 is aligned with tray track 3.

When the electromagnet 40 is controlled by the microprocessor 78 such that plunger 41 via finger 28 pivots the retaining means 19 with its blocking element 25 downwards and the blade 26 of retaining means 19 uncovers the sensor 27. Thus, exit 10 of tray track 3 is open for moving tray 5 onto transporter 12 by means of the tray movement member 14, arrows 100, FIG. 8.

Operation of the tray movement member 14 is effected via stepper motor 61, drive gear 62, toothed belt 63, guide roller 65, drive gear 66, toothed belt 49 and the idler 48, with the tray movement member 14 being connected to toothed belt 49. The stepper motor 61 is controlled by the microprocessor 78. An encoder wheel 67 mounted to shaft 88 and a sensor 68 are provided to determine the position of tray movement member 14 and thus tray 5 along the transporter 12. Upon rotation of shaft 88, the opaque and transparent sectors 72 of encoder wheel 67 generate pulses in sensor 68, the number of pulses being proportional to the path of movement of tray movement member 14 (see FIG. 6).

As soon as tray movement member 14 has pulled tray 5 with the test tubes 4 completely onto transporter 12, it is pivoted to the zero position 13 located adjacent to the tray tracks 3 and characterized by two slots 31. During this procedure the electromagnet 40 is de-energized and its plunger 41 returned to its home position by means of the helical spring 42. At the same time, retaining means 19 with the blocking element 25 is pivoted upwards back into the exit 10 of tray track 3 by means of leaf spring 29. Retaining means 19 thereby reaches its upper end position in which the blade 26 uncovers the sensor 27. It can now be detected whether a tray 5 is present in the tray track 3 or whether exit 10 of tray track 3 is empty. This is considered by the microprocessor in that it stops the program when a tray track 3 is occupied inadmissibly or even by two trays 5 at the same time and indicates this as an error on a display panel 79. Subsequently, tray 5 is moved to processing station 15 with the test tube predetermined in the program. In this station test tube 4 is first detected by detector means 22 and then body fluid is removed by means of the proboscis 21 of aspirator 20. Removal of the body fluids from the remaining test tubes 4 is effected in the same way. When all body fluids have been removed from the test tubes 4 of tray 5, transporter 12 pivots back to the initial tray track 3 and tray 5 is returned to the latter. Prior thereto, the retaining means 19 is again pivoted back by means of plunger 41 of electromagnet 40. Selection of further trays 5 from input station 1 and their transport to processing station 15 and back to the tray tracks 3 is performed in the same manner as described above.

Advantageously, control unit 76 offers blocking protection for the stepper motors 61 and 69 which, on the one hand, is realized by monitoring the rotary movement of the encoder wheel 67 by means of sensor 68 and, on the other, by comparing the pre-determined and the actual number of steps of the stepper motors 61 and 69. The blocked stepper motors are de-energized and an error is indicated on display 79. Undesired blocking may occur when a tray 5 of inadmissible height is inserted into one of the tray tracks 3 which is then pulled against the upper limiting edge of the passage 58 of wall 57. Blocking also occurs due to jamming of the base 83 of an inadmissible tray 5 between guide post 52 and transporter 12.

Furthermore, it is advantageous to control the attractive force of plunger 41 by a first low current pulse with a subsequent high current pulse and to reduce the release speed by means of reverse current pulses in order to minimize noise.

The functional procedure is changed by an appropriate development of the device in that, on the one hand, a scanner 18 is provided between input station 1 and processing station 15 for the patient's data available in the form of a bar code and in that on the other, a second processing station 16 is provided in the end position 17 for opening and closing the test tubes 4. This means that tray 5 equipped with test tubes 4 reaches the detector means 22 and the aspirator 20 only via the opening/closing means 16 and the scanner 18. Manual opening of the test tubes 4 and entering the patient's data by means of the keyboard 77 prior to inserting the trays 5 into the tray tracks 3 is thus eliminated, which results in an easier and more reliable operation.

The invention disclosed herein may be practiced in the absence of any element which is not specifically disclosed herein The invention has been described in detail with particular reference to certain preferred embodiments thereof, but it will be understood that variations and modifications can be effected within the spirit and scope of the invention.

What is claimed is:

1. In a device for transporting a tray of containers in an analyzer, the containers being filled with a body liquid, the device including an input station, a processing station, and a movable transporter for transporting trays from said input station to said processing station and back;
   wherein the improvement comprises said transporter having a pivot point about which it is pivoted and means for moving said transporter about said pivot point, and wherein said input station comprises a plurality of tray tracks arranged side by side, each with a central axis, said axes being disposed to intersect at a point vertically disposed above said pivot point.

2. A device according to claim 1, wherein said transporter comprises a housing which is pivoted about said pivot point, having a free end portion that extends as far as said tray tracks, and said moving means includes a stepper motor controlled by a microprocessor.

3. A device according to claims 1 or 2 wherein said moving means includes an arcuate rack and a gear connected to the stepping motor and to said rack.

4. A device according to claims 1 or 2 and further including means for zeroing said transporter to a zero position adjacent to the tray tracks.

5. A device according to claim 4, wherein said means for zeroing includes a slot in each of said tray tracks and a sensor to scan said slots to align said transporter with said slots in a zero position.

6. A device according to claim 1, wherein each tray track includes a retaining mean for an inserted tray, and means for disengaging said retaining means from an inserted tray when the transporter is aligned with the respective tray track.

7. A device according to claim 6, wherein the retaining means comprises a rocker having a first rocker arm and a blocking element for a tray present in the tray track and a second arm having a blade which in a first position when the tray track is empty uncovers a photosensor and in a second position when a tray is present in tray track covers the sensor.

8. A device according to claim 7, and further including means for moving the retaining means to a third position in which the tray is disengaged and the sensor is uncovered, said moving means including a second rocker arm attached to said rocker and having a finger which can be operated by means of a plunger of an electromagnet.

9. A device according to claim 8, and further including an electromagnet controlled by means of a microprocessor in response to the signals of the sensor, said electromagnet being mounted in said transporter.

10. A device according to claims 1 or 2, and further including a support plate provided in the area of the input station, on which slidingly rest supports connected to the transporter.

11. A device according to claim 10, wherein two of said supports are adjustable in height.

12. A device according to claims 1 or 2, wherein the transporter includes a tray engager which can be coupled with a tray and a microprocessor-controlled stepper motor for moving said engager.

13. A device according to claim 12, wherein the tray engager is slidingly guided on the transporter and includes a hook extending beyond the centerline of the transporter.

14. A device according to claim 12, further including a pulse generator for controlling the movement of the tray engager.

15. A device according to claim 14, wherein the pulse generator comprises a rotatable encoder wheel and a sensor.

16. A device according to claims 1 and 2 wherein said input station comprises a plurality of arranged exits wherein each said exit comprises an opening provided for the trays, said exits being arcuately arranged about said pivot point.

17. A device according to claim 16 wherein the pivoting transporter extends to an end position as far as the arcuately arranged exits of said input station.

18. A device according to claims 1, 2, or 3, and further including a patient's data scanner for reading data provided on containers arranged between said input station and said pivot point.

19. A device according to claim 12, wherein the transporter comprises a rectangularly shaped tubular housing which is substantially closed all-around and has an elongate opening in the area of a bottom portion, and wherein the tray engager reaches through the elongate opening and is connected to a toothed belt driven by a stepper motor.

20. A device according to claim 1 or 2, and further including T-shaped guide posts arranged on the transporter to guide trays.

21. A device according to claim 1, wherein the tray tracks are separated from each other at said input station by partitions.

22. A device according to claim 21, wherein the partitions are recessed from an outer border of said input station by a predetermined amount.

23. A device according to claim 22, wherein the partitions are wedge-shaped.

24. A device according to any of claims 21, 22, or 23, wherein the partitions are rounded at their outer ends.

25. A device according to claim 24 wherein the partitions are shorter in height than the trays.

26. A device according to claim 1, wherein the input station includes a wall and partitions which in the area of the tray tracks define passages which correspond to the shape and size of the trays.

27. A device according to claim 26, wherein the partitions have guide fins laterally extending into the tray tracks to hold a tray at a selected vertical height.

28. A device according to any of claim 1 or 2, wherein the transporter is at least twice as long as a tray.

29. A device according to claim 1, wherein the tray tracks are arranged on a support at said input station.

30. A device according to claim 29, wherein the tray tracks are countersunk in the support plate.

31. In a device for transporting a tray of containers in an analyzer, the containers being filled with a body liquid, the device including an input station, a processing station, and a movable transporter for transporting trays from said input station to said processing station and back;
wherein the improvement comprises said input station having a plurality of tray tracks each shaped to receive and support a tray, and at one end of each said track, a retaining means for a supported tray that is engageable with said transporter.

32. A device as defined in claim 31, wherein the retaining means comprises a rocker having a first rocker arm and a blocking element for a tray present in the tray track and a second arm having a blade which in a first position when the tray track is empty uncovers a photosensor and in a second position when a tray is present in tray track covers the sensor.

33. A device as defined in claim 32, and further including means for moving the retaining means to a third position in which the transporter is disengaged and the sensor is uncovered, said moving means including a second rocker arm attached to said rocker and having a finger which can be operated by means of a plunger of an electromagnet.

34. A device as defined in claim 33, and further including an electromagnet controlled by means of a microprocessor in response to the signals of the sensor, said electromagnet being mounted in said transporter.

* * * * *